(12) United States Patent
Dines

(10) Patent No.: US 10,149,814 B1
(45) Date of Patent: Dec. 11, 2018

(54) LACTIC ACID TOPICAL COMPOSITION AND METHOD OF FABRICATING THE SAME

(71) Applicant: Brett Dines, Dyer, IN (US)

(72) Inventor: Brett Dines, Dyer, IN (US)

( * ) Notice: Subject to any disclaimer, the term of this patent is extended or adjusted under 35 U.S.C. 154(b) by 361 days.

(21) Appl. No.: 15/092,375

(22) Filed: Apr. 6, 2016

(51) Int. Cl.
| | |
|---|---|
| *A61K 36/53* | (2006.01) |
| *A61K 36/00* | (2006.01) |
| *A61K 8/92* | (2006.01) |
| *A61K 8/365* | (2006.01) |
| *A61K 8/36* | (2006.01) |
| *A61K 8/49* | (2006.01) |
| *A61Q 19/00* | (2006.01) |

(52) U.S. Cl.
CPC ............ *A61K 8/922* (2013.01); *A61K 8/36* (2013.01); *A61K 8/365* (2013.01); *A61K 8/498* (2013.01); *A61Q 19/007* (2013.01); *A61K 2800/5922* (2013.01)

(58) Field of Classification Search
None
See application file for complete search history.

(56) References Cited

U.S. PATENT DOCUMENTS

2015/0342854 A1* 12/2015 Shibuya ............... A61Q 19/08
424/62

* cited by examiner

*Primary Examiner* — Christopher R Tate
*Assistant Examiner* — Randall O Winston
(74) *Attorney, Agent, or Firm* — FisherBroyles, LLP; Rob L. Phillips

(57) ABSTRACT

A Lactic Acid topical composition and method of fabricating the same. A Lactic Acid composition comprises: about 10% Lactic Acid by volume, Sodium Lactate, Tocopheryl Acetate (Vitamin E Acetate) and a cream base. For scenting Lavender Oil and/or Tea Tree Oil may be added. The Lactic Acid topical composition has a pH of 4.2 to 5 and more preferably 4.5 to 4.8 to enhance the effectiveness of the Lactic Acid topical composition.

10 Claims, 3 Drawing Sheets

LACTIC ACID TOPICAL COMPOSITION AND METHOD OF FABRICATING THE SAME

FIELD OF THE INVENTION

The embodiments of the present invention relate to an improved Lactic Acid Composition having a pH range of 4.2 to 5 and more preferably 4.5 to 4.8 and method of fabricating the same.

BACKGROUND

The skin is the largest organ of the integumentary system in humans. The skin covers the entire body and has a surface area of approximately 2 $m^2$ with a thickness ranging from 0.5 mm to 4 mm or more. The skin is involved with many functions, such as providing a protective barrier from the external environment (e.g., defending against microbial infection, inhibiting the entry of chemicals and toxins, preventing dehydration, etc.), regulating body temperature and producing vitamin D. The skin is also the most exposed organ and is subject to several physical and environmental stressors.

Up to 8.4 million people in USA or approximately 3.1% of the population suffer from, and manage, dry skin. The U.S. skin care market is estimated to reach $11 Billion in 2018. Many people suffer from dry, cracked skin (corneum) surrounding their nails due to cold, and dry weather and biting of their nails. Along with biting of their nails, people bite the skin surrounding their nails. Such biting can lead to painful rips and tears that have the potential to become infected. In dry winter weather, people tend to form cracked finger tips which can be quite painful.

Topical skin treatments exist in many forms, such as ointments, gels, creams, lotions, solutions, suspensions, foams and shampoos. The most commonly used topical compositions are semisolid dosage forms that include ointments, creams, lotions, and gels. However, prior art topical compositions suffer from drawbacks including ineffectiveness and side effects.

Thus, it would be advantageous to develop a more effective topical composition including the ability to treat and prevent dry skin.

SUMMARY

The embodiments of the present invention relate to a Lactic Acid topical composition and method of fabricating the same. In one embodiment, a Lactic Acid composition comprises: about 10% Lactic Acid by volume, Sodium Lactate, Tocopheryl Acetate (Vitamin E Acetate) and a cream base. For scenting, Lavender Oil and/or Tea Tree Oil may optionally be added.

Other variations, embodiments and features of the present invention will become evident from the following detailed description, drawings and claims.

DETAILED DESCRIPTION

Figure 1A:
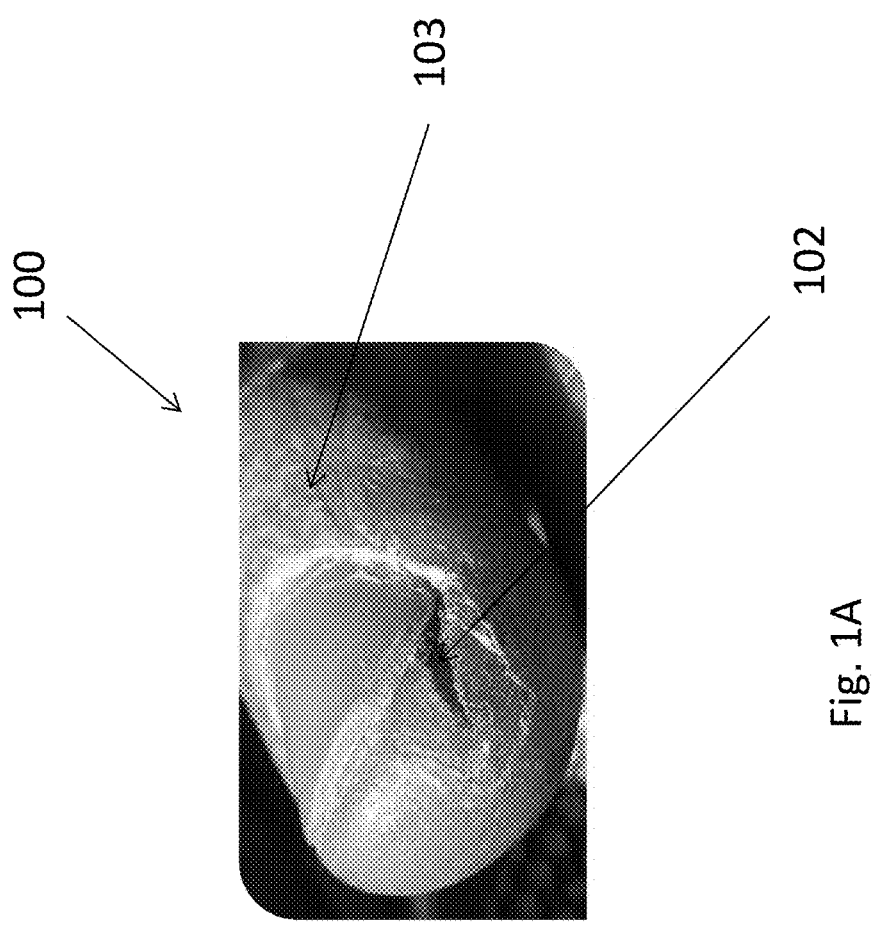
FIGS. 1A and 1B illustrate fingers displaying cracked, torn and dry skin.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

The extensibility of skin (corneum) depends upon its water content and upon its temperature. When the skin surface is exposed to cold or dry conditions, there must be a gradient of decreasing water content and temperature from the base of the stratum corneum to the surface. This means that the corneum surface tends to be less extensible than the deeper layers so that surface cracks and flaking occur more frequently than deep cracks or chapping.

One objective of skin cream and lotions is, therefore, to maintain a high corneum water content and extensibility so that skin cracking and flaking is less likely to occur. Several authors have shown that the water content of corneum depends upon the presence within the corneum of hygroscopic substances which can hold water in atmospheres of normal humidity. These hygroscopic substances are contained within the corneum's cells by the cell walls which are permeable to water but not to electrolytes such that hygroscopic substances cannot be extracted unless the cell wall is damaged. The water held by the hygroscopic substances maintains the extensibility of the corneum. The cell wall can be damaged by physical disruption, extracting its lipids with solvents or by prolonged treatment with detergents which also extract lipids. The loss of hygroscopic substances resulting from this damage reduces the water content and extensibility of corneum.

The knowledge of how the corneum normally holds water and maintains its extensibility enables one to postulate that extensibility of damaged corneum can be increased by adding hygroscopic substances and a number of skin preparations containing humectants such as glycerol and various mixtures simulating natural hygroscopic substances. However, with intact corneum, the natural hygroscopic substances are maintained in cells by cell walls. When hygroscopic materials are added to damaged corneum via solvents or detergents they tend to penetrate into the corneum cells, but are unlikely to be retained and are washed out when the skin is exposed to water.

The embodiments of the present invention serve to treat and prevent dry, cracked, torn and/or damaged skin while overcoming shortcomings of previous topical creams, ointments and related compositions.

Figure 1B:
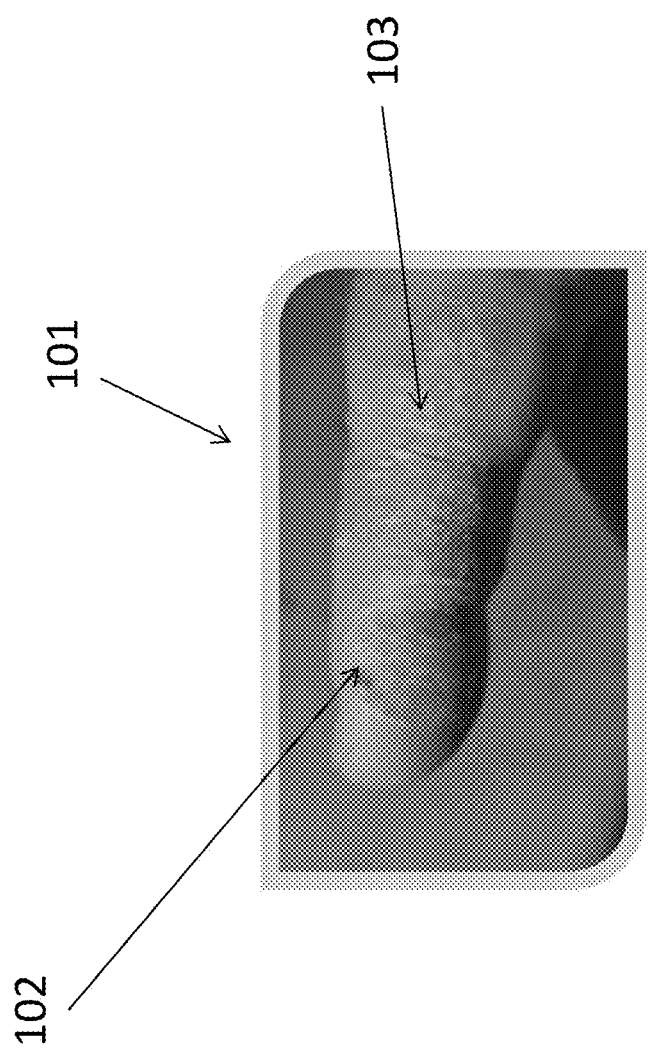

FIGS. 1A and 1B show examples of fingers 100, 101 with cracks 102 and dry areas 103 of the type suitable for treatment using the composition detailed herein.

The embodiments of the present invention relate to a finished topical composition includes at least Lactic Acid, Sodium Lactate, Tocopheryl Acetate (Vitamin E Acetate) and a cream base. As assembled, the finished topical composition detailed below has a pH range of 4.2 to 5 and more preferably a pH range of about 4.5 to 4.8. The pH range of 4.2 to 5 provides a cumulative and/or synergistic humectant effect resulting from the combination of Lactic Acid and Sodium Lactate forming a buffer system. The cumulative and/or synergistic humectant effect relates to improved water retention and extensibility in the corneum following hand washing. The pH buffer system of the weak acid/weak base maintains the pH of the Lactic Acid topical composition in a range of 4.2-5. Maintenance of the pH in the range allows both the Lactic Acid and the Sodium Lactate to exert their synergistic therapeutic humectant effects upon the skin for the purpose of yielding superior results. A pH greater than 5 stops the therapeutic humectant properties of Lactic Acid. Utilizing the weak acid/weak base buffer combination of Lactic Acid/Sodium Lactate in the prescribed quantities, results in a finished product's pH that is resistant to change from a range of 4.2 to 5.0. The buffer described herein retains its intended pH range and stability when using a variety of cream bases such as, set forth herein, Versapro™ and PenCream™.

In one embodiment, as detailed below, the finished topical composition comprises about 10% by volume Lactic Acid. Alternatively, the finished topical product may have from about 5%-15% by volume of Lactic Acid. In one embodiment, as detailed below, the finished topical composition comprises about 26% by volume Sodium Lactate. Alternatively, the finished topical composition may have from about 16%-36% by volume Sodium Lactate. In one embodiment, as detailed below, the finished topical composition comprises about 3551 IU/ounce of Tocopheryl Acetate (Vitamin E Acetate). Alternatively, the concentration of Tocopheryl Acetate may range from 3000 IU/ounce to 4000 IU/ounce. In one embodiment, as detailed below, the active ingredients, namely Lactic Acid, Sodium Lactate and Tocopheryl Acetate are combined with a cream base (e.g., Versapro™ manufactured by Medisca, Pencream™ manufactured by Humco Compounding, etc.). In one embodiment, as detailed below, the finished topical composition may include Tea Tree Oil and/or Lavender Oil for scenting.

Table 1 below shows an exemplary ingredient list for a topical cream according to the embodiments of the present invention. Table 1 shows quantities for a total batch of 960 grams of topical cream.

TABLE 1

| Ingredient | Quantity |
| --- | --- |
| Lactic Acid | 109.08 grams |
| Tocopheryl Acetate (Vitamin E) | 129.36 ml |
| Sodium Lactate | 420 grams |
| Cream Base (Versapro ™) | 306.8 grams |
| *Melalueca Alternifolia* (Tea Tree Oil) | 4 ml |
| Lavender Oil | 0.8 ml |

Table 2 below shows an exemplary ingredient list for another topical cream according to the embodiments of the present invention. Table 2 shows quantities for a 240 gram batch of topical cream.

TABLE 2

| Ingredient | Quantity |
| --- | --- |
| Lactic Acid | 27.27 grams |
| Tocopheryl Acetate (Vitamin E) | 32.34 ml |
| Sodium Lactate | 105 grams |
| Cream Base (Pencream ™) | 77.5 grams |
| *Melalueca Alternifolia* (Tea Tree Oil) | 1 ml |
| Lavender Oil | 0.2 ml |

In one embodiment, the Lactic Acid is Lactic Acid (L+) 88% supplied by Medisca. In one embodiment, the Sodium Lactate is Sodium Lactate 60% USP liquid supplied by Majestic Mountain Sage. In one embodiment, the Tocopheryl Acetate is Vitamin E (DL-) USP liquid supplied by Medisca. Those skilled in the art will recognize that other manufacturers may supply the active and inert ingredients. Those skilled in the art will further recognize that the ingredients may also have different optical rotations than those above.

The ingredients and quantities set forth in Tables 1 and 2 result in a finished topical composition having a pH between 4.2 and 5 (more specifically 4.5 to 4.8). The Lactic Acid and Sodium Lactate act as a buffer system. Lactic Acid is a known humectant, but has little humectant effect with a pH greater than 5. Sodium Lactate is a known humectant, but has diminishing effectiveness on natural hygroscopic substances as the pH of the substance is reduced below 5. The Lactic Acid and Sodium Lactate (i.e., weak acid/weak base) buffer system according to the embodiments of the present invention stabilizes the pH of the finished topical composition between 4.2 and 5 which synergistically enhances the effectiveness of the finished topical composition for dry, cracked, torn and/or rough skin. The ability to enable synergistic humectant properties of each of the active ingredients results in superior extensibility and corneum water content thus resulting in higher efficacy. The inability to synergistically enable both active ingredients using the pH buffer results in the known and existing limited effectiveness of the prior art compositions and products.

Figure 2:
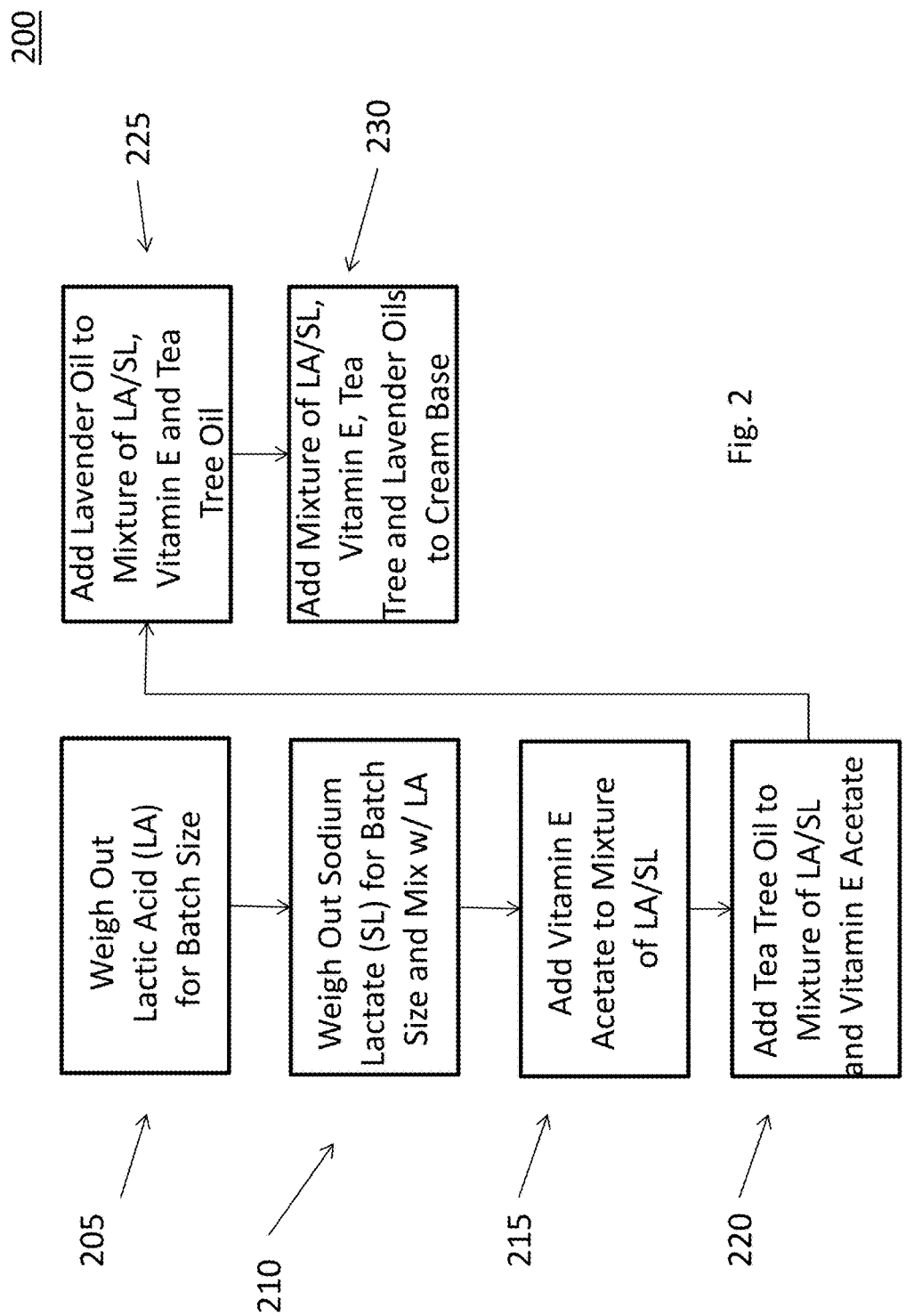
FIG. 2 illustrates a flow chart detailing a method of fabricating a Lactic Acid Topical according to the embodiments of the present invention.

FIG. 2 shows a flow chart 200 detailing a method of fabricating a Lactic Acid topical composition according to the embodiments of the present invention. At 205, Lactic Acid is weighed out for the desired batch size. At 210, Sodium Lactate is weighed out and added to the Lactic Acid. At 215, Vitamin E Lactate is added to the mixture of Lactic Acid and Sodium Lactate. At 220, Tea Tree Oil is added to the mixture of Lactic Acid, Sodium Lactate and Vitamin E Lactate. At 225, Lavender Oil is added to the mixture of Lactic Acid, Sodium Lactate, Vitamin E Lactate and Tea Tree Oil. At 230, the mixture of Lactic Acid, Sodium Lactate, Vitamin E Lactate, Tea Tree Oil and Lavender Oil is added to the cream base thereby completing the fabrication process. While Tea Tree Oil and Lavender Oil are disclosed, any aromatic compound or scent may be used to create a pleasant odor or impart aroma therapeutic properties. Aromatic ingredients are optional. Moreover, while no therapeutic claims are being made about Tea Tree Oil, those skilled in the art recognize that Teat Tree Oil is a known homeopathic/alternative medicine aromatic oil.

Although the invention has been described in detail with reference to several embodiments, additional variations and modifications exist within the scope and spirit of the invention as described and defined in the following claims.

I claim:

1. A topical composition comprising:
   about 5% to 15% of Lactic Acid;
   about 16% to 36% of Sodium Lactate;
   Vitamin E Acetate;
   a cream base; and
   wherein the topical composition has a pH of between about 4.2 and 5 such that said Lactic Acid and said Sodium Lactate both provide a therapeutic effect to skin of a user.

2. The topical composition of claim 1 further comprising Tea Tree Oil.

3. The topical composition of claim 1 further comprising Lavender Oil.

4. The topical composition of claim 1 wherein topical composition has a pH of between 4. 5 and 4.8.

5. The topical composition of claim 1 wherein a 960 gram batch of said topical composition comprises the following ingredients and quantities:

| Ingredient | Quantity |
| --- | --- |
| Lactic Acid | 109.08 grams |
| Tocopheryl Acetate | 129.36 ml |
| Sodium Lactate | 420 grams |
| Cream Base | 306.8 grams |
| *Melalueca Alternifolia* (Tea Tree Oil) | 4 ml |
| Lavender Oil | 0.8 ml. |

6. The topical composition of claim 1 wherein a 240 gram batch of said topical composition comprises the following ingredients and quantities:

| Ingredient | Quantity |
| --- | --- |
| Lactic Acid | 27.27 grams |
| Tocopheryl Acetate | 32.34 ml |
| Sodium Lactate | 105 grams |
| Cream Base | 77.5 grams |
| *Melalueca Alternifolia* (Tea Tree Oil) | 1 ml |
| Lavender Oil | 0.2 ml. |

7. A topical composition comprising:
about 10% of Lactic Acid;
about 26% of Sodium Lactate;
Vitamin E Acetate;
a cream base; and
wherein the topical composition has a pH of between about 4.2 and 5 such that said Lactic Acid and said Sodium Lactate both provide a therapeutic effect to skin of a user.

8. The topical composition of claim 7 further comprising Tea Tree Oil.

9. The topical composition of claim 7 further comprising Lavender Oil.

10. The topical composition of claim 7 wherein topical composition has a pH of between 4.5 and 4.8.

\* \* \* \* \*